United States Patent [19]
Jackson et al.

[11] Patent Number: 5,502,651
[45] Date of Patent: Mar. 26, 1996

[54] POTENTIOPHOTOMETRIC FIBRINOGEN DETERMINATION

[76] Inventors: R. David Jackson; Wallace E. Carroll, both of 1556 San Leandro La., Santa Barbara, Calif. 93108

[21] Appl. No.: 236,330

[22] Filed: May 2, 1994

[51] Int. Cl.$^6$ .................................................. G01N 33/86
[52] U.S. Cl. ................... 364/509; 364/413.07; 364/497; 435/13; 422/73; 436/69; 356/39
[58] Field of Search ........................... 364/509, 497, 364/499, 413.07, 413.08, 413.09, 496; 436/69, 34, 164; 356/39; 422/73, 72; 435/13

[56] References Cited

U.S. PATENT DOCUMENTS

| | | | |
|---|---|---|---|
| 3,905,769 | 9/1975 | Carroll et al. | 436/69 |
| 4,047,890 | 9/1977 | Eichelberger et al. | 364/413.09 |
| 4,252,536 | 2/1981 | Kishimoto et al. | 356/39 |
| 4,289,498 | 9/1981 | Baughman et al. | 436/34 |
| 4,720,787 | 1/1988 | Lipscomb | 364/413.07 |
| 5,197,017 | 3/1993 | Carroll et al. | 364/497 |
| 5,350,676 | 9/1994 | Oberhardt et al. | 435/13 |

*Primary Examiner*—James F. Trammell
*Attorney, Agent, or Firm*—John F. A. Earley; John F. A. Earley, III

[57] ABSTRACT

An apparatus and a method are disclosed for measuring the concentration of fibrinogen that contributes to the clotting of blood. The apparatus utilizes a potentiophotometer that provides an output which is directly indicative of the fibrinogen concentration in the blood sample. The present invention takes into account the prothrombin time which is defined as the time between the injection of a reagent into a sample of the blood being measured and the time of the clotting or coagulation. The present invention relies on the knowledge that a specified minimum amount of fibrinogen needs to be present in the blood sample in order to detect the forming of a clot. After the detection of the specified minimum amount, the invention then relies on monitors for the fibrinogen concentration to decrease to a value which is less than the specified minimum amount.

32 Claims, 3 Drawing Sheets

FIG. 5 ptotensiophotometric fibrinogen

POTENTIOPHOTOMETRIC FIBRINOGEN DETERMINATION

BACKGROUND OF THE INVENTION

1. Field of the Invention

This invention relates to measuring the coagulation rate of fluids, and more particularly concerns measuring prothrombin time, the time between the injection of a thromboplastin reagent into a sample of blood plasma being tested and the beginning of the formation of the plasma clot.

2. Description of the Prior Art

Prothrombin time indicates the level of prothrombin in a plasma sample and is a measure of the coagulation response of a patient. It is sometimes desired to extend the prothrombin time by having a patient take medicine in an attempt to prevent the formation of blood clots which could cause a coronary artery clot and heart attack or travel through the blood stream to the brain and cause a stroke. One such medicine, coumadin, requires a periodic check of the prothrombin time to make sure the time for starting coagulation is extended, but not extended too far so as to cause internal bleeding.

This invention relates to the inventions disclosed in U.S. Pat. Nos. 3,905,769 ('769) of Sep. 16, 1975 and 5,197,017 ('017) dated Mar. 23, 1993, both issued to Wallace E. Carroll and Richard D. Jackson, and both of which are incorporated herein by reference. The present application discloses an improvement over the methods and apparatus shown and described in both earlier patents.

SUMMARY OF THE INVENTION

The invention measures prothrombin time and fibrinogen by an improved method of measuring the optical density (O.D.) of a fluid sample, particularly blood plasma, and this improved method may be referred to as the "clot slope" method. Whole blood consists of cellular elements (red and white blood cells), platelets and plasma. This invention works only with plasma. The invention provides a method and apparatus for developing digital electrical signals representing voltage values which are linearly related to the optical density (O.D.) of a semi-transparent fluid aliquot of citrated human plasma using a potentiophotometer. Since the optical density of the plasma is directly proportional to fibrinogen concentration, the method and apparatus of the present invention measure fibrinogen concentration. As is well known, fibrinogen is a protein manufactured by the liver and is essential to the clotting of blood.

The method and apparatus of the present invention are also used to measure prothrombin time simultaneously with measuring fibrinogen concentration. As is also well known, prothrombin is one of several proteins manufactured in the liver that contribute to clotting, and the prothrombin time is the time between the injection of a reagent into the blood sample being tested and the beginning of formation of a clot. The prothrombin time indicates the level of prothrombin in a blood sample and is a measure of the coagulation response of a patient.

The method and apparatus of the present invention also measure the time duration of the clotting process from its initiation to its termination. The determination of the level of fibrinogen concentration of a sample under test is accomplished during the measurement of the clotting process and within a period of time that is substantially less than prior art methods and apparatus that are used to measure fibrinogen concentration and prothrombin time.

DETAILED DESCRIPTION

Figure 1:
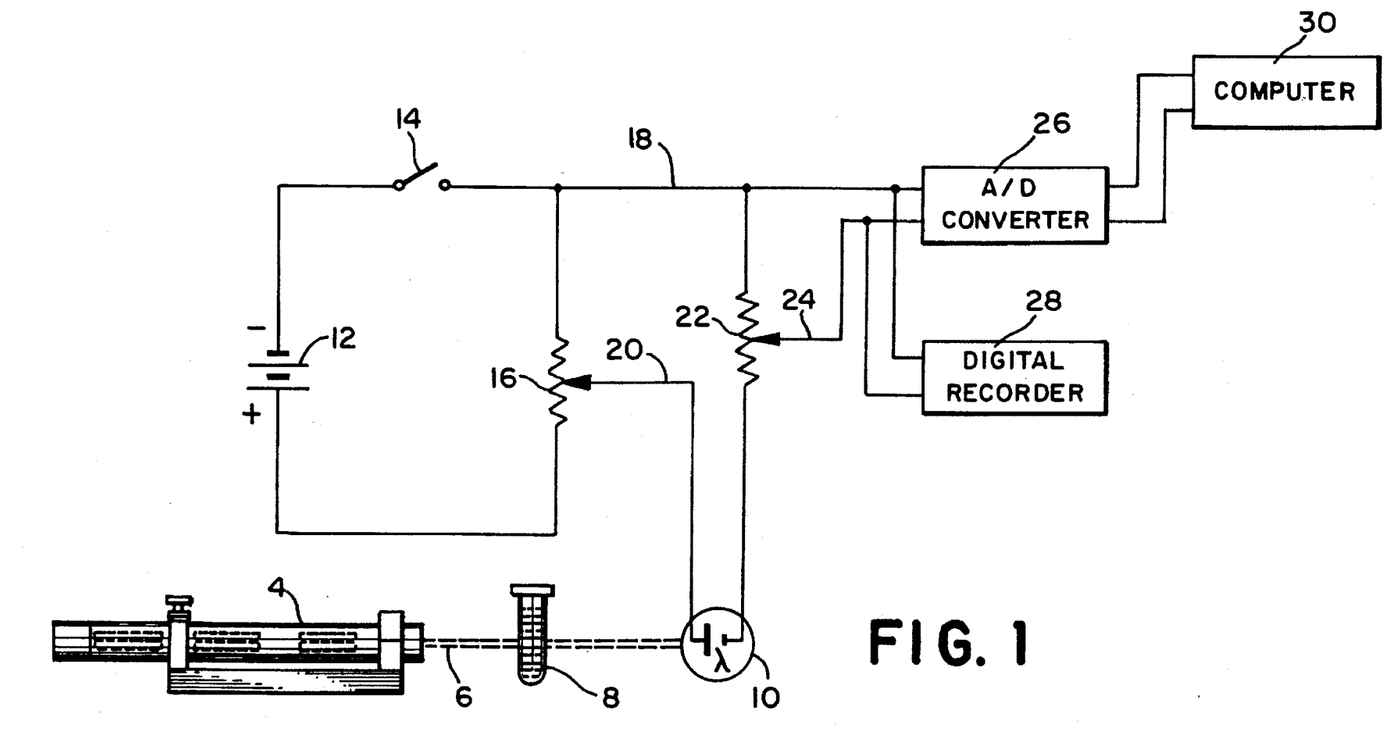
FIG. 1 is a diagram of potentiophotometric (hereinafter sometimes referred to as "POTENS PLUS") fibrinogen determination apparatus generally similar to that shown in FIG. 1 of both U.S. Pat. Nos. 3,905,769 and 5,197,017, with the output of the analog/digital (A/D) converter of this invention being applied to a computer.

Referring to the drawings, there is shown in FIG. 1 a light source 4 which may be a low power gas laser producing a beam of light 6 which passes through a sample test tube or cuvette 8 and is received by detection means which is preferably a silicon or selenium generating photocell 10 (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means photocell 10, the positive output of detection means photocell 10 being connected to the wiper 20 of variable resistor 16 so that the voltage produced by the variable voltage DC source opposes the voltage produced by the detection means photocell 10. The negative output of detection means photocell 10 is connected through variable resistor 22 to line 18. Thus, the voltage across variable resistor 22 is the difference between the voltage produced by the variable voltage DC source and the voltage produced by the photovoltaic cell 10. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

In the present invention, wiper 24 is placed at a position to give a suitable output and is not varied during the running of the test. The output between line 18 and wiper 24 is delivered to an A/D converter 26 and digital recorder 28. As is known, the A/D converter 26 and the digital recorder 28 may be combined into one piece of equipment and may, for example, be a device sold commercially as ADALAB-PC and ADAPT available from Interactive Microware, Inc., State College, Pennsylvania. The signal across variable resistor 22 is an analog signal and hence the portion of the signal between leads 18 and wiper 24, which is applied to the A/D converter 26 and digital recorder 28, is also analog. A computer 30 is connected to the output of the A/D converter 26, is preferably IBM compatible, and is programmed in a manner described hereinafter.

The practice of the present invention preferably includes fibringoen (FBG) standard solutions and control solution wherein the fibrinogen standard solutions act as dormant references to which solutions analyzed by the present invention are compared, whereas the control solution acts as a reagent that is used to control a reaction related to the present invention. The fibrinogen standards include both high and low solutions, whereas the control solution is particularly used to control clotting times and fibrinogens of blood samples.

A fibrinogen (FBG) solution of 10 g/l was prepared from a cryopreciate. The cryopreciate was prepared by freezing plasma, letting the plasma thaw in a refrigerator and then, as known in the art, expressing off the plasma so as to leave behind the residue cryopreciate. The gathered cryopreciate contained a substantial amount of both desired fibrinogen (FBG) and Factor VIII (antihemophila globulin) along with other elements that are not of particular concern to the present invention. The 10 g/l fibrinogen solution, after further treatment, served as the source for the high FBG standard. A 0.5 g/l fibrinogen solution was then prepared by a 1:20 (10 g/l/20 =0.5 g/l) dilution of some of the gathered cryopreciate to which was added a Owren's Vernon Buffer (pH 7.35) and which, after further treatment, served as the source of the low FBG standard. Then, 1 ml of each of the high (10 g/l) and low (0.5 g/l) sources of the fibrinogen standards were added to 1 ml of normal human plasma (so the human plasma could clot), and this addition respectively yielded 6.38 g/l and 1.5 g/l high and low fibrinogen (FBG) standards, used in the practice of the present invention for analyzing samples of citrated blood under test.

As is known, the addition of the reagent Thromboplastin C serves as a coagulant to cause clotting to occur within a sample of citrated blood under test and contained in a test tube 8. As the clotting occurs, the A/D converter counts and produces a digital value of voltage at a predetermined period, such as once every 0.05 or 0.01 seconds. As more fully described in U.S. Pat. No. 5,197,017 ('017), these voltage values are stored and then printed by the recorder as an array of numbers, the printing being from left to right and line by line, top to bottom. There are typically one hundred numbers in the five groups representing voltage values every second and hence, one line represents one-fifth of a second in time (20×0.01 seconds). Individual numbers in the same column are twenty sequential numbers apart. Hence, the time difference between two adjacent numbers in a column is one-fifth of a second. The significance of these recorded values may be more readily appreciated after a general review of the operating principles of the present invention illustrated in FIG. 2.

Figure 2:
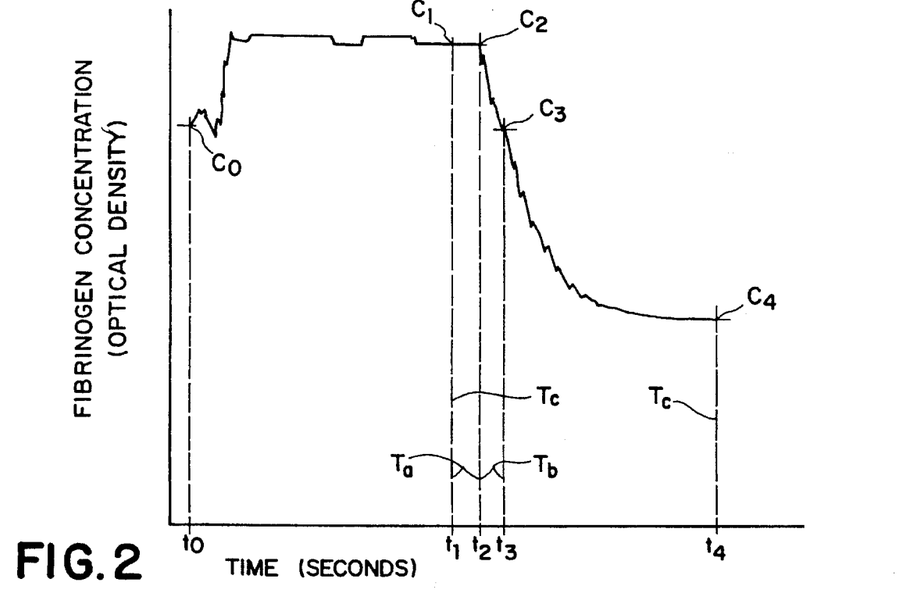
FIG. 2 is a plot of the various phases of the fibrinogen concentration occurring in a typical plasma clotting process.

FIG. 2 illustrates the data point locations of the clotting curve related to the present invention. In general, FIG. 2 illustrates a "clot slope" method of the present invention which measures the concentration of the fibrinogen (FBG) in the plasma that contributes to the clotting of the plasma and uses the potentiophotometer of FIG. 1 to provide an output voltage signal that is directly indicative of the fibrinogen concentration in the plasma sample under test contained in a test tube 8. The quantities given along the Y-axis of FIG. 2 are values (+ and –) that may be displayed by the digital recorder 28. As will be more fully described, the "clot slope" method comprises detection of the rate or the slope of the curve associated with the formation of fibrin from fibrinogen. The "clot slope" method takes into account the pro-thrombin time which is typically defined as the time duration between the injection of a reagent, such as thromboplastin, into the plasma and the corresponding instant of time when the clotting process begins. As seen in FIG. 2, at time $t_o$, corresponding to a concentration $c_o$, the thromboplastin reagent is introduced into the blood plasma which causes a disturbance to the composition of the sample which, in turn, causes the optical density of the plasma to increase momentarily. After the injection of the reagent (the time of which is known, as to be described, by the computer 30), the digital quantity of the recorder 28 rapidly increases and then levels off in a relatively smooth manner but does encounter some step-like changes and then continues along until the quantity $c_1$ is reached at a time $t_1$. The optical density of the quantity $c_1$ directly corresponds to a specified minimum amount of fibrinogen that must be present for a measuring system, such as the circuit arrangement of FIG. 1, to detect that a clot is being formed. Further, all the quantities shown in FIG. 2 are of optical densities that are directly correlatable to fibrinogen concentration values. The critical quantity $c_1$, may vary from one clot detection system to another, but for the potentiophotometer system of FIG. 1, this minimum is defined by units of mass having a value of about 0.05 grams/liter (g/l).

The detection of this first predetermined quantity $c_1$ is shown in FIG. 2 to occur at an instant time $t_1$ which is the start of the clotting process being monitored by the clot slope method of the present invention. The time $t_1$ is the beginning point of the fibrinogen formation, that is, it is the point that corresponds to the beginning of the acceleration of the fibrinogen conversion that lasts for a predetermined time, preferably about 1.5 seconds. This $t_1$ point is determined by a real time analysis of the optical density data accumulated during testing. The time duration of at least 1.5 seconds allows a sufficient amount of delay time to eliminate any false responses due to noises created by initial mixing of the reagent into the sample or bubbles within the sample under test. This 1.5 second duration helps determine the beginning point ($t_l$) of the fibrinogen conversion in spite of any bubbles or artifacts that might be present for short durations. These noise producers might be erroneously interpreted as early clots and might lead to a correspondingly false response by the instrument performing the measuring. However, it should be noted, the conversion of fibrinogen actually starts shortly after the thromboplastin is injected in the sample, because at that time thromboplastin combines with prothrombin and calcium in the blood sample to form thrombin which, in turn, converts the fibrinogen to a fibrous substance, fibrin, that causes clot formation.

The acceleration of the fibrinogen conversion that occurs within the 1.5 second duration, is shown in FIG. 2 as a first time period $T_a$. The first time period $T_a$ is defined by the first quantity $c_1$ and a second $c_2$ occurring at a time $t_2$, wherein $c_2$ has a value equal to at least $c_1$. The acceleration of the fibrinogen conversion continues until a time $t_3$ having a corresponding quantity $c_3$. The time $t_3$, as well as the quantity $c_3$, is of critical importance because it is the point of maximum acceleration of the fibrinogen to fibrin conversion and is also the point where deceleration of conversion begins. The times $t_3$ and $t_2$ define a second time period $T_b$ which has a typical value of 1.5 seconds. The deceleration of conversion continues until a quantity $c_4$ is reached at a time $t_4$. The time $t_4$ is the point where the deceleration of conversion corresponds to a value which is less than the required amount of fibrinogen that was present in order to start the fibrinogen conversion process. Thus, because the desired fibrinogen conversion is no longer in existence, the time $t_4$ represents the ending point of the fibrinogen conversion as defined by the present invention. The fibrinogen conversion has a starting point of $t_1$ and an ending point of $t_4$. These times $t_1$ and $t_4$ define a third period $T_c$. The significance of these points ($t_1$, and $t_4$) are not the times at which they occur, but rather the difference in the optical density of the quantities $c_1$ and $c_4$ occurring at the times $t_1$ and $t_4$. This difference is defined herein as the delta optical density for the clot slope method of the present invention. The clot slope method that gathers typical data as shown in FIG. 2 has four critical parameters. The first is that the initial delta optical density of substance being analyzed should be greater than about 0.05 g/l in order for the circuit arrangement of FIG. 1 to operate effectively. Second, the acceleration (fibrinogen conversion defined by $T_a$) should be increasing for a minimum period of about 1.5 seconds so as to overcome any false reactions created by bubbles. Third, the total delta optical density (defined by the difference in quantities $c_1$ and $c_4$) should be at least three (3) times the instrument value in order to perform a valid test, i.e., (3) (0.05 g/l)=0.15 g/l. Fourth, and finally, the "clot slope" end point of the fibrinogen conversion is defined as the point ($t_4$) where the deceleration of conversion becomes less than the instrument value of about 5 mg/dl that is used to detect the clot point ($t_1$). As with most clot detection systems, a specific amount of fibrinogen needs to be present in order to detect a clot forming. Adhering to the four given parameters allows the present invention to determine a specific quantity of fibrinogen. In order for that specific amount of fibrinogen to be determined, it is first necessary to detect a clot point ($t_1$). After that clot point ($t_1$) is detected, it logically follows that when the fibrinogen conversion becomes less than the specific amount (about 5 mg/dl for the circuit arrangement of FIG. 1), the end point ($t_4$) of the fibrinogen conversion has been reached.

In the practice of this invention, a series of 5552 data points, such as those shown in FIG. 2, were collected and analyzed with the results of such being given in Table 1.

TABLE 1

| TIMES | OPTICAL DENSITY (DIGITAL RECORDER 28 VALUE) | CONCEN-TRATION | TIME OF OCCURRENCE (IN SECONDS) RELATIVE TO $t_0$ |
|---|---|---|---|
| $t_0$ | −903 | $c_0$ | — |
| $t_1$ | 859 | $c_1$ | 14.31 |
| $t_2$ | 677 | $c_2$ | 15.81 |
| $t_3$ | −424 | $c_3$ | 17.31 |
| $t_4$ | −1657 | $c_4$ | 27.85 |

From the quantities given in Table 1, it may be seen that a typical delta optical density ($c_1$−$c_4$) is 2516, a typical duration $t_1$−$t_4$ (see $T_c$ of FIG. 2) is about 13.54 (27.85−14.31) seconds and a typical time ($t_1$) of the occurrence of clot point after the injection ($t_o$) of a reagent is 14.31 seconds.

The gathering, storing, and manipulation of the data shown in Table 1 and generally illustrated in FIG. 2, is primarily accomplished by computer 30 of FIG. 1 that receives digital voltage values converted, by the A/D converter 26, from analog voltage quantities of the photocell 10 detection means.

The preferable IBM,compatible computer 30 of FIG. 1 stores and manipulates these digital values corresponding to the fibrinogen concentration data of FIG. 2 and is preferably programmed as follows:

(a) with citrated blood, such as described above in the test tube 8, the computer 30, as well as the recorder 28, sequentially records voltage values for a few seconds before injection of thromboplastin. As previously discussed, thromboplastin is one of the factors in the human body that causes blood to clot. Prothrombin is another. Fibrinogen is yet another. Before injection of the thromboplastin, the output from the A/D converter 26 is relatively constant. When thromboplastin is injected into the blood in test tube 8, a significant and abrupt change occurs in the recorded voltage values of both the computer 30 and the recorder 28. This abrupt is recognized by both the recorder 28 and, more importantly, the computer 30 which uses such recognition to establish $t_o$ discussed with reference to FIG. 2. The computer 30 may be programmed so as to correlate the digital quantities of the A/D converter to the analog output of the detector means photocell 10 which, in turn, is directly correlatable to the fibrinogen concentration g/l of the sample of blood discussed with reference to FIG. 2.

(b) Following the recording of digital quantities representative of the fact that thromboplastin had been injected (see $t_o$ of FIG. 2), the computer 30 may be programmed to look for a digital quantity representative of the previously discussed critical quantity $c_1$, and when such occurs, record its instant time $t_1$. The time span between $t_o$ and $t_1$ is the prothrombin time and has a normal duration of about 12 seconds, but maybe greater than 30 seconds.

(c) Following the detection of the critical quantity $c_1$, the computer 30 may be programmed to detect for the acceleration of fibrinogen conversion within the defined time period $T_a$, having a typical duration of 1.5 seconds. The parameters of this time period $T_a$ are its beginning which is defined by the occurrence ($t_1$) of the first predetermined quantity $c_1$ and its end which is defined by the second predetermined quantity $c_2$ occurring at time $t_2$. The first predetermined time period $T_a$ has a typical range of about 12 to about 30 seconds as measured from $t_o$. The computer 30 is also programmed to detect the maximum acceleration quantity $c_3$ and its time of occurrence $t_3$ (having a typical value of 1.5 seconds after $t_2$). These two times $t_2$ and $t_3$ define the time duration $T_b$. Furthermore, the computer detects the quantity $c_4$ occurring at time $t_4$ so as to define the time duration $T_c$. The time period $T_a$ may exceed but may not be less than the typical 1.5 second duration. The duration of the time between the occurrence ($t_1$) of the quantity $c_1$, and the occurrence ($t_2$) of the quantity $c_2$ is not fixed. It is only important that the rate of fibrin formation increase for at least 1.5 second following the occurrence of ($t_1$). (d) Following the detection of the acceleration of fibrinogen conversion, the computer 30 is programmed to detect for a deceleration of the fibrinogen conversion, wherein the fibrinogen concentration decrease from its third predetermined quantity $c_3$ to a fourth predetermined quantity $c_4$ having a value which is about equal but less than the first quantity $c_1$. The time duration from the instant time of the detection of the first quantity $c_1$ to the instant time of the detection of the fourth quantity $c_4$, defines the third period $T_c$.

(e) The computer 30 manipulates the collected data of (a); (b); (c) and (d) above, to determine the clotting time based on the principle that if a required amount (e.g., 0.05 g/l) of fibrinogen concentration $c_1$ is first necessary to detect a clot point ($t_1$); then when the fibrinogen concentration ($c_4$) becomes less than the required amount $c_1$, which occurs at time ($t_4$), the fibrinogen end point has been reached. More particularly, the required fibrinogen concentration $c_1$ is the starting point of fibrinogen conversion of the clotting process and the less than required fibrinogen concentration $c_4$ is the end point of the fibrinogen conversion of the clotting process. Thus, the duration of the fibrinogen conversion of the clotting process for the clot slope method of the present invention is defined by the time period between $t_1$ and $t_4$ and is generally indicated in FIG. 2 as $T_c$.

(f) The computer 30 also manipulates the collected data of (a), (b), (c), (d) and (e) above, to determine the total delta optical density between the quantities $c_1$ and $c_4$. Furthermore, the computer determines the maximum acceleration quantity $c_3$. More particularly, the computer 30 may have an appropriate program, that is known in the art, to search backwards, sometimes referred to as a regression technique, through the data gathered during clotting time to determine its maximum acceleration of the fibrinogen conversion.

The present invention may be carried out in one of two ways, both with equally correct results. The first way is to determine the fibrinogen concentration directly from the voltages, sensed by the A/D converter 26 and delivered to the computer 30, created by the disturbance to the optical density of the test sample in response to the injection of the reagent thromboplastin, discussed with reference to FIG. 2. The second way is to compare these disturbances to those occurring for samples having known fibrinogen concentration.

For carrying out this second way, two plasma samples of known but different fibrinogen concentration, one high and one low, are placed separately in the test tube 8 and separately tested to produce respective sets of digital voltage values. The method used for the testing is similar to that already described with reference to FIG. 2, with the exception that the voltages of the A/D converter 26 are utilized rather than the digital display values of the digital recorder 28. However, it should be recognized that the delta optical density, e.g., 2516 of Table 1, displayed by digital recorder 28 is directly correlatable to the digital voltage provided by the A/D converter 26. For such testing, the samples that are used to produce the first set of digital voltage values have the previously discussed high fibrinogen concentration of 6.38 g/l and low fibrinogen concentration of 1.5 g/l. Each of the high and low concentrations produce a delta voltage quantity $V_d$ which may be further described with reference to FIG. 3.

Figure 3:
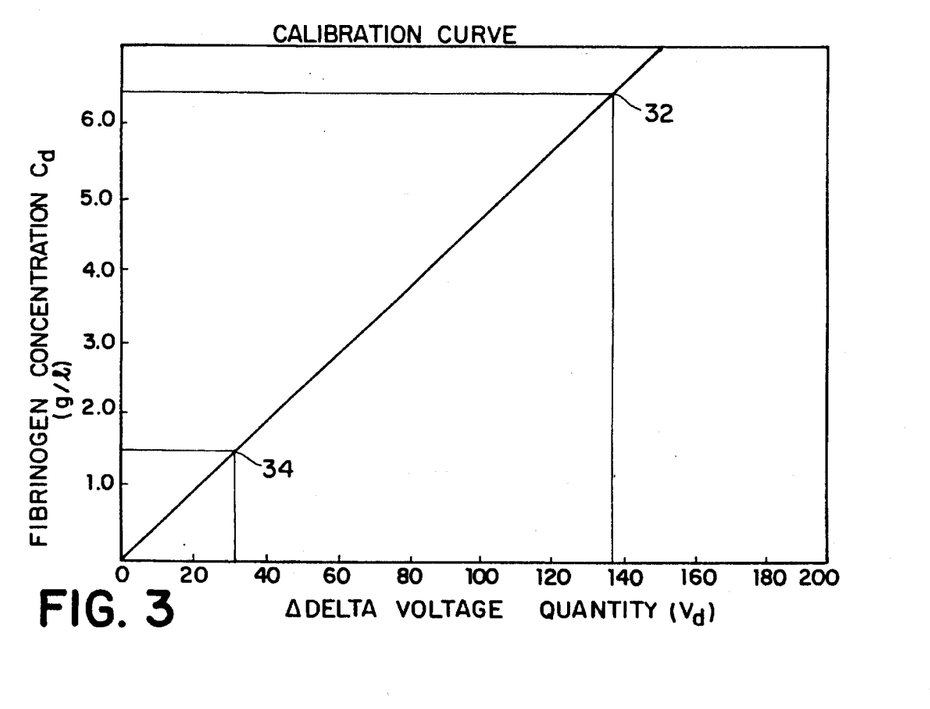
FIG. 3 is a calibration curve used in the practice of the present invention to determine fibrinogen concentrations of blood samples.

The delta voltage quantity $V_d$ forms the X axis of FIG. 3, whereas the high and low fibrinogen concentrations are given as $c_d$ which is shown as being along the Y axis of FIG. 3. The high concentration $c_d$ of 6.38 g/l produces a delta voltage $V_d$ quantity of 137 shown as a first calibration point 32, whereas the low concentration $c_d$ of 1.5 g/l produces a delta voltage $V_d$ quantity of 32 shown as a second calibration point 34.

The next step involved with the testing of standard specimens is to draw a straight line between the two calibration points 32 and 34 developed above, and to project the line linearly in both directions. This line is now a calibration "curve," which can be used to determine further fibrinogen concentrations $c_d$ in plasma samples of unknown fibrinogen concentration.

Once the calibration curve of FIG. 3 is established, unknown fibrinogen concentrations are easily determined. For example, an unknown fibrinogen concentration may produce a delta voltage quantity $V_d$ of 37. By using the calibration curve of FIG. 3, it is easily determined that this $V_d$ quantity of 37 corresponds to a delta fibrinogen concentration $c_d$ of 1.85 g/l. Similarly, a delta voltage quantity $V_d$ of 113 corresponds to a delta fibrinogen concentration $c_d$ of 5.4 g/l. Instead of reading the values of unknown fibrinogen concentration from the curve in FIG. 3, it is contemplated that the computer 30 may be used to correlate the unknown values to known values by using, e.g., look-up tables.

As indicated previously, and as discussed with reference to FIG. 2, the instant time at which the quantity $c_1$ is detected identifies the beginning of fibrinogen conversion of the clotting process, whereas the instant time at which the quantity $c_4$ is detected identifies that the ending of the fibrogen conversion of the clotting process. The clotting time may vary from a normal time of about 14 seconds to a time of about greater than 30 seconds. Similarly, the time which elapses between the injection of thromboplastin $t_o$ and the instant time $t_1$ of $c_1$ is the prothrombin time.

It should be appreciated that the circuit arrangement of FIG. 1, sometimes referred to as a POTENS PLUS or a POTENTIOPHOTOMETRIC FIBRINOGEN DETERMINATION apparatus, and the "clot slope" method of the present application are useful not only in determining the fibrinogen concentration of unknown blood samples or other liquid samples, but also in determining prothrombin time simultaneously with the measurement of fibrinogen concentration.

It should be noted that after clotting begins, i.e., $t_1$ (see FIG. 2), the changes in optical density (and thus the fibrinogen concentrations) are relatively stable until $c_2$ is reached, wherein the optical density increases in a somewhat linear manner until it extends past $c_3$ and then begins to follow an exponential decay curve that eventually flows into the fourth predetermined quantity $c_4$, previously discussed with reference to FIG. 2.

Three different sets of comparative results were obtained between the method such as that described in U.S. Pat. No. 5,197,017 ('017) and herein termed "clot+60 seconds" and the clot slope method of the present invention. The comparisons included clot+60 seconds testing that was done at the same time as the clot slope method testing, previously described with reference to FIG. 2.

The clot+60 seconds testing included the injection of the reagent, thromboplastin, and noting the occurrence of the beginning of the clotting process. Concurrently, the digital values at the recorder 28 and corresponding fibrinogen concentration were recorded. Four (4) seconds were allowed to pass to establish a baseline fibrinogen concentration having a corresponding digital value on the recorder 28 of 871. The clot+ 60 seconds testing then noted the time of occurrence of the clot time (corresponds to the $t_1$, (14.31) and $c_1$ quantities of FIG. 2), and then waited an additional 60 seconds to record a final digital value being −1706. Such clot+60 seconds testing resulted in a delta optical density of 2577 (871−(−1706)) and its accumulated time, after the injection of the reagent, was 74.31 (14.31+60) seconds. From this testing is seen that the delta optical density (2577) substantially matches the delta optical density (2516) of FIG. 2 obtained by the clot slope method of the present invention.

The second set of comparison testing comprised the results of 266 tests related to both the clot+60 seconds method and the clot slope method of the present invention accomplished by a computer program that may be expressed by the below syntax statements:

M=READPRN ($f_1$); clot+60 seconds=$M^{<o>}$; clot slope= $M^{<1>}$

N=rows (clot+60 seconds); i=0 . . . N−1; a=(clot+60 seconds, clot slope) b=intercept (clot+60 seconds, clot slope) c=correlation coefficient (Pearson's r)

Where M is a matrix of two columns, N is the number of tests compared and has the value of 266, "a" is the slope of least-squares regression line of the data points, "b" is the y-intercept of the least-squares regression of the data points, and "c" is the correlation coefficient (Pearson's r) of the data points.

Figure 4:
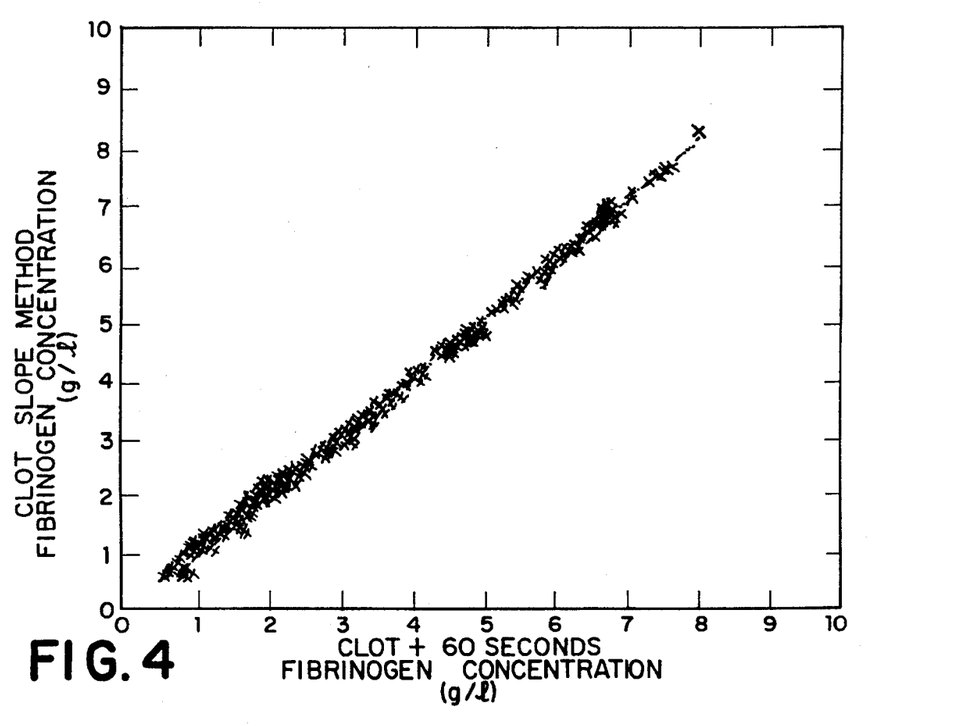
FIGS. 4 and 5 depict the results of linear regression analyses performed on the delta fibrinogen concentrations obtained by the process similar to that described in U.S. Pat. No. 5,197,017 and those obtained by the process of the present invention.
Figure 5:
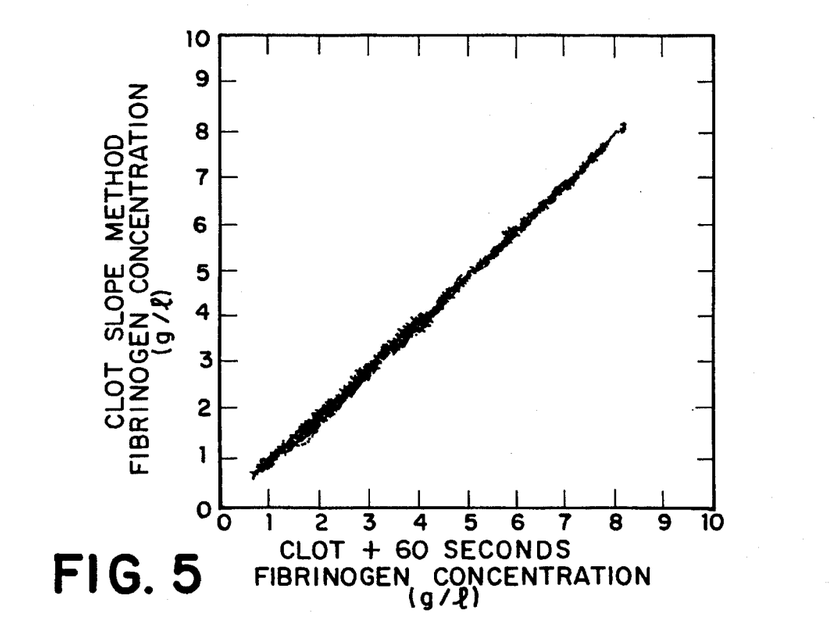

The results obtained by computer are illustrated in FIG. 4 which has a Y axis giving the fibrinogen concentration (g/l) obtained by the clot slope method, and an X axis giving the fibrinogen concentration (g/l) obtained by the clot+60 seconds method. These results may be expressed by the above parameters a; b; and c as respectively having values of 1; −0.014; and c=0.999. The third set of comparison testing included an additional 112 tests analyzed by the computer program described with reference to FIG. 4 and having the results illustrated in FIG. 5 which has the same X and Y axes described for FIG. 4. The results of the testing illustrated in FIG. 5 may be expressed by the above parameters a; b; and c as respectively having values of 0.998; −0.035; and 0.999. From the above three sets of comparison testing it should be noted that the clot+60 seconds and the clot slope methods yield substantially the same results, but the clot slope method does so in a time duration which is about 50 seconds less than that of the clot+60 seconds. More particularly, the clot slope method obtains a typical delta fibrinogen concentration in 27.85 seconds, whereas the clot+60 seconds requires 74.31 (14.31+60) seconds to obtain a typical delta fibrinogen.

The practice of the present invention provides for a "clot slope" method yielding results comparable to prior art methods, but obtains the correct results in about one-third of the time required by the reliable prior-art method described in the '017 patent.

We claim:

1. A method of testing a liquid sample comprising the steps of:

(a) developing a series of analog electrical voltage signals having voltage amplitudes proportional to the optical density of the liquid sample;

(b) converting the developed analog voltage signals into a series of digital voltage value signals;

(c) injecting a coagulant into a liquid sample, thereby producing an abrupt change in the optical density of the liquid sample, said abrupt change producing an abrupt change in the amplitude of the electrical analog signals which, in turn, produces an abrupt change in the value of digital voltage signal;

(d) recording the instant time of said abrupt change in said value of said digital voltage signal;

(e) monitoring said voltage digital signal values for a first predetermined minimum significant quantity $c_1$;

(f) recording the instant time and the value of the voltage digital signal of said first predetermined quantity $c_1$;

(g) monitoring for a differential change in the voltage digital signal values that include a second predetermined quantity $c_2$, which is at least equal to said first predetermined quantity, a third predetermined quantity $c_3$ and a fourth predetermined quantity $c_4$, said first ($c_1$) and second ($c_2$) predetermined quantities occurring within a first predetermined time period $T_a$, said second $c_2$ and third $c_3$ predetermined quantities occurring within a second predetermined time period $T_b$, and said first $c_1$ and said fourth $c_4$ predetermined quantities occurring within a third predetermined time period $T_c$;

(h) recording the instant time and voltage digital signal value for each of said first ($c_1$), second ($c_2$), third ($c_3$) and fourth ($c_4$) predetermined quantities, said first predetermined time period $T_a$ being defined by the time difference between the instant times of said first ($c_1$) and second ($c_2$) predetermined quantities, said second predetermined time period $T_b$ being defined by the time difference between the instant times of said second ($c_2$) and third ($c_3$) predetermined quantities, and said third predetermined time period $T_c$ being defined by the time difference between the instant times of said first ($c_1$) and fourth ($c_4$) predetermined quantities;

(i) subtracting the value of the voltage digital signal of said first predetermined quantity $c_1$ from the value of said digital signal of said fourth predetermined quantity $c_4$ to derive a delta voltage value signal, said delta voltage value having a value which exceeds the digital voltage value of said first predetermined quantity $c_1$ by at least threefold;

(j) using the foregoing steps to develop a delta voltage value signal for each of two calibrating samples having known values of optical density in units of mass;

(k) determining the relationship between the known values of optical density of the aforesaid two calibrating samples and the corresponding developed delta signals of said two calibrating samples;

(l) developing a delta voltage signal for a test sample having unknown optical density in units of mass using the steps indicated hereinabove; and (m) determining the optical density of the test sample in units of mass from its developed delta voltage signal using the mean relationship between the two calibrating samples of known optical density in units of mass and the voltage values of the corresponding developed voltage delta signals to derive, from the delta voltage signals developed for the test sample of unknown optical density, the optical density of the test sample in units of mass.

2. A method according to claim 1, wherein the liquid sample is blood plasma.

3. A method according to claim 1, wherein the developed delta voltage signal is proportional to the fibrinogen concentration in the test sample.

4. A method according to claim 3, wherein a chart is used having delta voltage signals plotted along one axis and fibrinogen concentration in units of mass plotted along the other, wherein the delta voltage signals for each of two samples of known fibrinogen concentration are marked opposite the known value, in units of mass, of fibrinogen concentration, wherein a straight line is drawn between the two marks and projected linearly in both directions to form a calibration curve, and wherein the delta voltage signal developed for the test sample of unknown fibrinogen concentration is marked on the calibration curve and the value in units of mass of fibrinogen concentration corresponding thereto is determined.

5. A method according to claim 1, wherein the coagulant which is injected into the sample is thromboplastin.

6. A method according to claim 3, wherein said first determined quantity $c_1$ is representative of a fibrinogen concentration of about 0.05 g/l, and wherein said first predetermined time period $T_a$ is about 1.5 seconds.

7. A method according to claim 1, wherein said beginning of said first predetermined time period occurs within a range of about 12 seconds to above about 30 seconds as measured from said instant time of said injecting of said coagulant.

8. A method according to claim 7, wherein said termination of said second predetermined time period $T_b$ occurs within a time of about 1.5 seconds as measured from said ending of said first predetermined time period.

9. A method according to claim 1, wherein the time duration between the time instant of said first predetermined quantity, $c_1$, and the time instant of said fourth predetermined quantity, $c_4$, constitutes a fibrinogen conversion time.

10. A method according to claim 1 in which the analog electrical voltage signal is developed by transmitting a light beam through a sample and sensing the variations in light passing therethrough to develop corresponding variations in the electrical signal produced.

11. A method of measuring the optical density of a liquid sample comprising the steps of:

(a) developing a series of analog electrical voltage signals having voltage amplitudes proportional to the optical density of the liquid sample;

(b) converting the developed analog voltage signals into a series of digital voltage value signals;

(c) injecting a coagulant into a liquid sample, thereby producing an abrupt change in the optical density of the liquid sample, said abrupt change producing an abrupt change in the amplitude of the electrical analog signals which, in turn, produces an abrupt change in the value of digital voltage signal;

(d) recording the instant time of said abrupt change in said value of said digital voltage signal;

(e) monitoring said voltage digital signal values for a first predetermined minimum significant quantity $c_1$;

(f) recording the instant time and the value of the voltage digital signal of said first predetermined quantity $c_1$;

(g) monitoring for a differential change in the voltage digital signal values that include a second predetermined amount $c_2$, which is at least equal to said first predetermined quantity ($c_1$), a third predetermined quantity ($c_3$) and a fourth predetermined quantity ($c_4$), said first ($c_1$) and second ($c_2$) predetermined quantities occurring within a first predetermined time period $T_a$, said second ($c_2$) and third ($c_3$) predetermined quantities occurring within a second predetermined time period $T_b$, and said first ($c_1$) and said fourth ($c_4$) predetermined quantities occurring within a third predetermined time period $T_c$;

(h) recording the instant time and voltage digital signal value for each of said second ($c_2$), third ($c_3$) and fourth ($c_4$) predetermined quantities, said first predetermined time period $T_a$ being defined by the time difference between the instant times of said first ($c_1$) and second ($c_2$) predetermined quantities, said second predetermined time period $T_b$ being defined by the time difference between the instant times of said second ($c_2$) and third ($c_3$) predetermined quantities and said third predetermined time period $T_c$ being defined by the time difference between the instant times of said first ($c_1$) and fourth ($c_4$) predetermined quantities;

(i) subtracting the value of the voltage digital signal of said first predetermined quantity $c_1$ from the value of said digital signal of said fourth predetermined quantity $c_4$ to derive a delta voltage value signal, said delta voltage value having a value which exceeds the digital voltage value of said first predetermined quantity $c_1$ by at least threefold;

(j) developing a delta voltage signal for a test sample having unknown optical density in units of mass using the steps indicated hereinabove; and (k) determining the optical density of the test sample in units of mass from its developed delta voltage signal.

12. A method according to claim 11, wherein the liquid sample is blood plasma.

13. A method according to claim 11, wherein the developed delta voltage signal is proportional to the fibrinogen concentration in the sample.

14. A method according to claim 11, wherein the coagulant which is injected into the sample is thromboplastin.

15. A method according to claim 11, wherein said first determined quantity $c_1$ is representative of a fibrinogen concentration of about 0.05 g/l and wherein said first predetermined time period $T_a$ is about 1.5 seconds.

16. A method according to claim 11, wherein said beginning of said first predetermined time period occurs within a range of about 12 seconds to above about 30 seconds measured from said instant time of said injecting of said coagulant.

17. A method according to claim 16, wherein said termination of said second predetermined time period occurs within about 1.5 seconds as measured from said ending of said first predetermined time period $T_a$.

18. A method according to claim 11, wherein the time duration between the time instant of said first predetermined quantity $c_1$ and the time instant of said fourth predetermined quantity $c_4$ constitutes a fibrinogen conversion time.

19. A method according to claim 11 in which the analog electrical voltage signal is developed by transmitting a light beam through a plasma sample and sensing the variations in light passing therethrough to develop corresponding variations in the electrical signal produced.

20. Apparatus for measuring the optical density of a liquid sample comprising:

(a) means including a light source, a test tube, a photocell, a battery, and a variable resistor all for developing an analog electrical voltage signal having an amplitude proportional to the optical density of a liquid sample;

(b) means including an A/D converter, and a computer both cooperating for converting and recording the developed analog signal into a series of digital voltage signal values;

(c) means for injecting a coagulant into the liquid sample, thereby producing an abrupt change in the optical density of the liquid sample, said abrupt change producing a minimum abrupt significant change of at least a preselected amount in the voltage values which, in turn, produces an abrupt change in the value of the digital voltage signals;

(d) means for recording the instant time of said abrupt change in said value of said digital voltage signal;

(e) means, including said computer, for monitoring said voltage digital signal values for a value representative of a first predetermined minimum significant quantity, $c_1$;

(f) means for recording the instant time and the value of the voltage digital signal of said first predetermined quantity $c_1$;

(g) means, including said computer, for monitoring said voltage digital signal values to determine a differential change that include a second predetermined quantity $c_2$, which is at least equal to said first predetermined quantity, $c_1$, a third predetermined quantity, $c_3$, and a fourth predetermined quantity $c_4$, said first ($c_1$) and second ($c_2$) quantities occurring within a first predetermined time period $T_a$, said second $c_2$ and third $c_3$ predetermined quantities occurring within a second predetermined time period $T_b$, and said first $c_1$ and said fourth $c_4$ predetermined quantities occurring within a third predetermined time period $T_c$;

(h) means for recording the instant time and voltage digital signal value for each of said second ($c_2$), third ($c_3$) and fourth ($c_4$) predetermined quantities, said first predetermined time period $T_a$ being defined by the time difference between the instant times of said first ($c_1$) and second ($c_2$) predetermined quantities, said second predetermined time period $T_b$ being defined by the time difference between the instant times of said second ($c_2$) and third ($c_3$) predetermined quantities, and said third predetermined time period $T_c$ being defined by the time difference between the instant times of said first ($c_1$) and fourth ($c_4$) predetermined quantities;

(i) means for subtracting the value of the voltage digital signal of said first predetermined quantity, $c_1$, from the digital signal of said fourth predetermined quantity $c_4$ to derive a delta voltage value signal, said derived delta voltage value being of a value which exceeds the digital voltage value of said first predetermined quantity $c_1$ by at least threefold;

(j) a chart showing a calibration curve which passes through the delta voltage signals obtained for two calibrating samples, whereby the relationship between the two calibrating samples of known optical density in units of mass and the voltage value of the developed delta signals corresponding thereto is used to derive, from the delta voltage signal developed for the test sample of unknown optical density, the value of optical density in units of mass of the liquid sample.

21. The apparatus according to claim 20, wherein the liquid sample is blood plasma.

22. The apparatus according to claim 20, wherein the developed delta voltage signal is proportional to fibrinogen concentration in the sample.

23. The apparatus according to claim 20, wherein the coagulant which is injected into the liquid sample is thromboplastin.

24. An apparatus for measuring the optical density of a liquid sample comprising:

(a) means including a light source, a test tube, a photocell, a battery, and a variable resistor all for developing an analog electric voltage signal having an amplitude proportional to the optical density of a liquid sample;

(b) means including an A/D converter and a computer both cooperating for converting and recording the developed analog signal into a series of digital voltage signal values;

(c) means for injecting a coagulant into a liquid sample, thereby producing an abrupt change in the optical density of the liquid sample, said abrupt change producing a change in the amplitude of the electrical analog signals, which, in turn, produces an abrupt change in the value of said digital voltage signals;

(d) means for recording the instant time of said abrupt change in said value of said digital voltage signal;

(e) means for monitoring said voltage digital signal values for a first predetermine minimum significant quantity $c_1$;

(f) means for recording the instant time and the value of the voltage digital signal of said first predetermined quantity $c_1$; (g) means, including said computer, for monitoring said voltage digital signal values to determine a differential change in the voltage digital signal values that include a second predetermined quantity $c_2$, which is at least equal to said first predetermined quantity ($c_1$), a third predetermined quantity, $c_3$, and a fourth predetermined quantity $c_4$, said first ($c_1$) and second ($c_2$) predetermined quantities occurring within a first predetermined time period $T_a$, said second, $c_2$, and third, $c_3$, predetermined quantities occurring within a second predetermined time period $T_b$, and said first, $c_1$, and said fourth, $c_4$, predetermined quantities occurring within a third predetermined time period $T_c$;

(h) means for recording the instant time and voltage digital signal value for each of said second ($c_2$), third ($c_3$) and fourth ($c_4$) predetermined quantities, said first predetermined time period $T_a$ being defined by the time difference between the instant times of said first ($c_1$) and second ($c_2$) predetermined quantities, said second predetermined time period $T_b$ being defined by the time difference between the instant time of said second ($c_2$) and third ($c_3$) predetermined quantities, and said predetermined time period $T_c$ being defined by the time difference between the instant times of said first ($c_1$) and fourth ($c_4$) predetermined quantities;

(i) means for subtracting the value of the voltage digital signal of said first predetermined quantity, $c_1$, from the value of said digital signal of said fourth predetermined quantity, $c_4$, to derive a delta voltage value signal, said delta voltage value being of a value which exceeds the digital voltage value of said first predetermined quantity $c_1$ by at least threefold;

(j) means for determining the optical density of the test sample in units of mass from its developed delta voltage signal.

25. The apparatus according to claim 24., wherein the liquid sample is blood plasma.

26. The apparatus according to claim 24, wherein the developed delta voltage signal is proportional to fibrinogen concentration in the sample.

27. The apparatus according to claim 24, wherein the coagulant which is injected into the sample is thromboplastin.

28. The apparatus according to claim 24, wherein said first determined quantity $c_1$ is representative of a fibrinogen concentration of about 5 mg/dl and wherein said first predetermined time period $T_a$ is about 1.5 seconds.

29. The apparatus according to claim 24, wherein said beginning of said first predetermined time period occurs within a range of about 12 seconds to above about 30 seconds as measured from said instant time of said injecting of said coagulant.

30. The apparatus according to claim 24, wherein said termination of said second predetermined time period $T_b$ occurs about 1.5 seconds as measured from said ending of said first predetermined time period.

31. The apparatus according to claim 24, wherein the time duration between the time instant of said first predetermined quantity, $c_1$, and the time of said fourth predetermined quantity, $c_4$, constitutes a fibrinogen conversion time.

32. The apparatus according to claim 24 in which the analog electrical voltage signal is developed by transmitting a light beam through a plasma sample and sensing the variations in light passing therethrough to develop corresponding variations in the electrical signal produced.

* * * * *